United States Patent
Moses et al.

(10) Patent No.: US 7,748,493 B2
(45) Date of Patent: Jul. 6, 2010

(54) RESPIRATION STIMULATION

(75) Inventors: Ron L. Moses, Bellaire, TX (US);
Marianna Tessel, Palo Alto, CA (US);
Boris Dubnov, Petach-Tiqwa (IL);
Halina Dubnov, legal representative, Kfar-Saba (IL); Mordehai Tessel, Kfar-Saba (IL)

(73) Assignee: Zmed Technologies, Inc., Bellaire, TX (US)

( * ) Notice: Subject to any disclaimer, the term of this patent is extended or adjusted under 35 U.S.C. 154(b) by 170 days.

(21) Appl. No.: 11/763,189

(22) Filed: Jun. 14, 2007

(65) Prior Publication Data

US 2008/0009915 A1 Jan. 10, 2008

Related U.S. Application Data

(60) Provisional application No. 60/804,706, filed on Jun. 14, 2006.

(51) Int. Cl.
*A61N 1/36* (2006.01)
(52) U.S. Cl. .......................... 181/129; 607/42; 361/312
(58) Field of Classification Search .................. 607/42, 607/55
See application file for complete search history.

(56) References Cited

U.S. PATENT DOCUMENTS

| | | | |
|---|---|---|---|
| 3,802,417 A | 4/1974 | Lang | |
| 3,998,209 A | 12/1976 | Macvaugh | |
| 4,064,869 A | 12/1977 | Defares et al. | |
| 4,146,885 A | 3/1979 | Lawson, Jr. | |
| 4,644,330 A | 2/1987 | Dowling | |
| 4,657,026 A | 4/1987 | Tagg | |
| 4,715,367 A | 12/1987 | Crossley | |
| 4,788,533 A | 11/1988 | Mequignon | |
| 4,813,427 A | 3/1989 | Schlaefke et al. | |
| 5,295,490 A | 3/1994 | Dodakian | |
| 5,477,867 A | 12/1995 | Balkanyi | |
| 5,645,054 A | 7/1997 | Cotner et al. | |
| 5,853,005 A | 12/1998 | Scanlon | |
| 6,093,158 A | 7/2000 | Morris | |
| 6,142,950 A | 11/2000 | Allen et al. | |
| 6,155,985 A | 12/2000 | Ruton | |
| 6,190,328 B1 | 2/2001 | Ruton et al. | |
| 6,213,955 B1 | 4/2001 | Karakasoglu et al. | |
| 6,314,324 B1 * | 11/2001 | Lattner et al. | 607/42 |

(Continued)

FOREIGN PATENT DOCUMENTS

WO       8704630 A1    8/1987

OTHER PUBLICATIONS

Carley, D. W. et al., "Respiratory and Arousal Responses to Acoustic Stimulation." Chest. 112(6): 1567-1571, 1997.

(Continued)

*Primary Examiner*—Carl H Layno
*Assistant Examiner*—Alyssa M Alter
(74) *Attorney, Agent, or Firm*—Haynes and Boone LLP

(57) ABSTRACT

An automated respiration stimulation apparatus comprising a detector configured to measure a respiratory cycle of a user and a stimulator configured to automatically apply a stimulation to the user's acoustic nerve to interrupt a disturbance in the respiratory cycle of the user in response to the detection of the disturbance as indicated by the respiratory cycle measurements of the detector.

20 Claims, 5 Drawing Sheets

U.S. PATENT DOCUMENTS

| | | |
|---|---|---|
| 6,329,352 B1 | 12/2001 | Meyer et al. |
| 6,368,287 B1 | 4/2002 | Hadas |
| 6,544,199 B1 | 4/2003 | Morris |
| 6,748,275 B2 | 6/2004 | Lattner et al. |
| 6,928,324 B2 | 8/2005 | Park et al. |
| 6,935,335 B1 | 8/2005 | Lehrman et al. |
| 6,989,744 B2 | 1/2006 | Proebsting |
| 7,025,729 B2 | 4/2006 | de Chazal et al. |
| 7,115,097 B2 | 10/2006 | Johnson |
| 2003/0195588 A1 | 10/2003 | Fischell et al. |
| 2003/0199945 A1 | 10/2003 | Ciulla |
| 2005/0107838 A1* | 5/2005 | Lovett et al. .......... 607/17 |
| 2005/0197588 A1 | 9/2005 | Freeberg |
| 2005/0274387 A1 | 12/2005 | MacKen |
| 2005/0277821 A1 | 12/2005 | Payne, Jr. |
| 2005/0279367 A1 | 12/2005 | Klemperer |
| 2005/0283039 A1 | 12/2005 | Cornel |
| 2005/0283089 A1 | 12/2005 | Sullivan et al. |
| 2006/0102171 A1 | 5/2006 | Gavish |
| 2006/0145878 A1 | 7/2006 | Lehrman et al. |
| 2006/0173257 A1 | 8/2006 | Nagai et al. |
| 2006/0174897 A1 | 8/2006 | Sarkisian |
| 2006/0187067 A1 | 8/2006 | Simpson |
| 2006/0206014 A1 | 9/2006 | Ariav |

OTHER PUBLICATIONS

Basner, R.C. et al., Effect of Induced Transient Arousal on Obstructive Apnea Duration. J. Appl. Physiol. 78(4): 1469-1476, 1995.

Carlson, D.M. et al., Acoustically Induced Cortical Arousal Increases Phasic Pharyngeal Muscle and Disphragmatic EMG in NREM Sleep. J. Appl. Physiol. 76(4): 1553-9, 1994.

Khoo, Michael C. K. et al., "Ventilatory Dynamics During Transient Arousal from NREM Sleep: Implications for Respiratory Control Stability." J. Appl. Physiol. 80(5): 1475-84, 1996.

Badr, M. Safwan et al., "Ventilatory Response to Induced Auditory Arousals During NREM Sleep." Sleep. 20(9): 707-14, 1997.

Schwartz, D.J. And Moxley, P. "On the Potential Clinical Relevance of the Length of Arousals from Sleep in Patients with Obstructive Sleep Apnea." J. Clin. Sleep Med. 2(2): 175-80, 2006.

Pressler, G.A. et al., "Detection of Respiratory Sounds at the External Ear." IEEE Transactions on Biomedical Engineering. 51(12): 2089-96, 2004. (Abstract Only).

Kingshott, R.N. et al., "Does Arousal Frequency Predict Daytime Function." Eur Respir J. 12; 1264-1270, 1988.

Stepanski, E.J. "The Effect of Sleep Fragmentation on Daytime Function." Sleep. 25(3): 268-276, 2002.

Stradling, J.R. et al., "Prevalence of sleepiness and its relation to autonomic evidence of arousals and increase aspiratory effort in a community based population of men and women." J Slleep Res. 9; 381-388, 2000.

* cited by examiner

RESPIRATION STIMULATION

CROSS-REFERENCE TO RELATED APPLICATIONS

This application claims the benefit of U.S. Provisional Application No. 60/804,706, entitled "RESPIRATION STIMULATION APPARATUS," filed Jun. 14, 2006, the disclosure of which is hereby incorporated herein by reference.

This application is also related to commonly-assigned U.S. application Ser. No. 11/424,011, entitled "RESPIRATION STIMULATION APPARATUS," filed Jun. 14, 2006, the disclosure of which is hereby incorporated herein by reference.

BACKGROUND

Embodiments of the present disclosure generally relate to respiration. More specifically, the present disclosure relates to apparatus and methods for stimulating respiration during sleep.

A clinical pathologic entity called Sleep Apnea Syndrome (SAS) affects many individuals around the world. SAS is currently generally characterized by repetitive stops of respiration. SAS may cause severe disturbances of sleep, and may have deleterious effects on mental activities, such as intellectual performance, memory, and behavior. Further, SAS is known as one of the causes of cardiovascular diseases, increased blood pressure (hypertension), stroke, heart arrhythmia, and conduction disturbances, which may lead to fatal cardiac arrest. SAS is especially dangerous in patents having chronic lung and heart diseases.

A common means of physiologic protection against SAS is usually arousal from sleep and the restoration of normal breathing as a result of temporary normalization of the cortical neural control of respiration. However, as expected, these repetitive arousals result in fragmented and disturbed sleep.

Current treatments of SAS have been limited to mechanical stenting of the airway via CPAP (continuous positive airway pressure) devices and oral appliances, as well as surgical procedures aimed at removing, reducing, repositioning, or stiffening tissue in the upper airway. CPAP and oral devices currently have only a 50%-60% compliance rate because of patients' feelings of claustrophobia, nasal stuffiness, and inconvenience related to these devices' awkward and cumbersome equipment. Moreover, surgical treatments are usually very painful, require the use of general anesthesia, and can have severe complications. In the medical literature, surgical interventions are, at best, about 60-70% effective at curing SAS.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
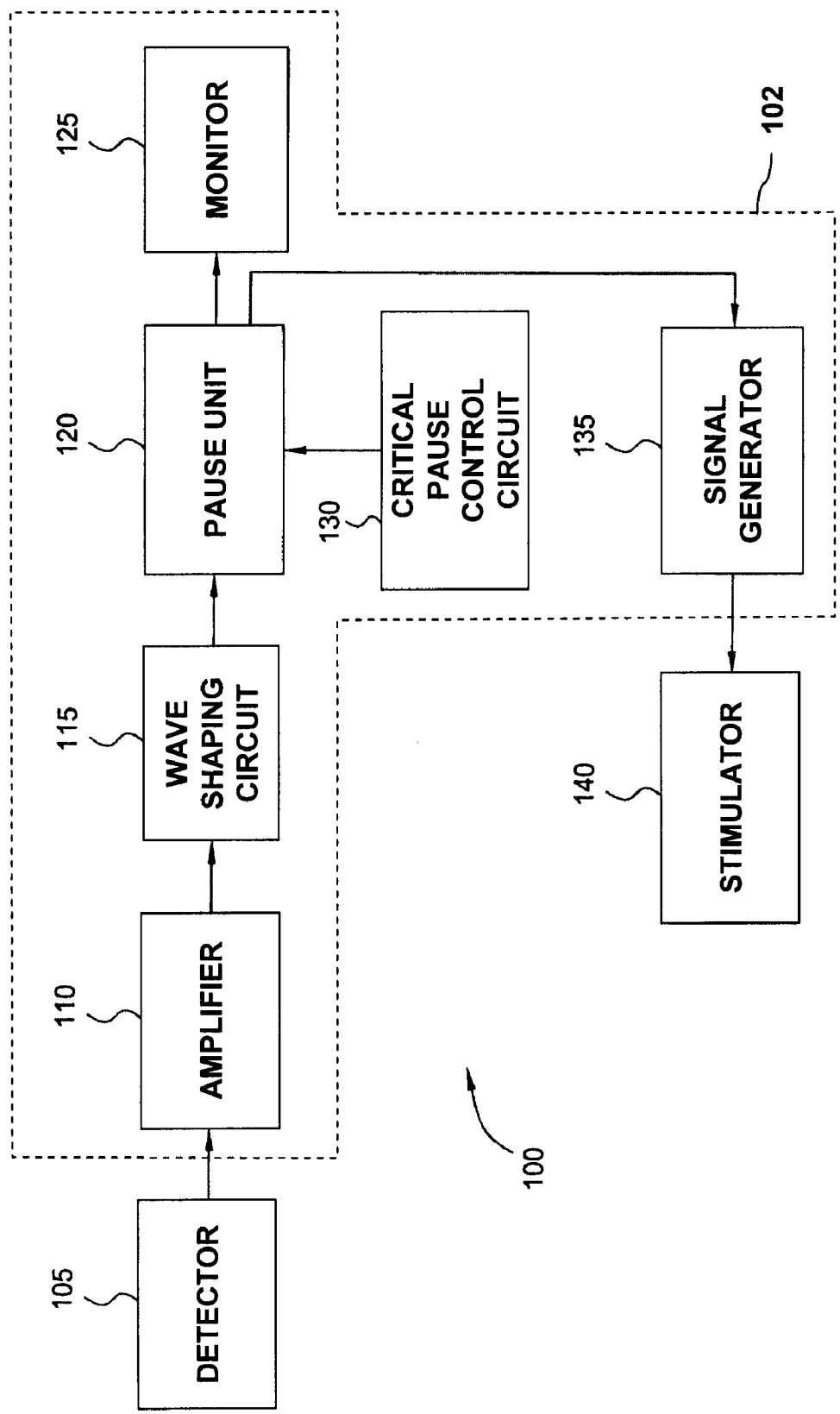
FIG. 1 is a block diagram of a device for acoustic stimulation of respiration in accordance with one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Apparatus within the scope of the present disclosure may be powered by any suitable power source, such as a battery, docking station, power in the wall, multiple batteries, and/or others. However, although merely for the sake clarity, such power source is not depicted in the figures. Nonetheless, those skilled in the pertinent art will recognize that any power scheme is within the scope of the present disclosure.

FIG. 1 is a block diagram of an automated apparatus 100 for acoustic stimulation of respiration in accordance with one or more aspects of the present disclosure. As illustrated in FIG. 1, the apparatus 100 includes a sensor or detector 105. The detector 105 is configured to measure parameters related to the respiratory cycle of the user, and then provide an output signal indicative of the user's respiratory cycle.

For example, the detector 105 may be or comprise a thermistor and/or other air-flow detector, which is affixable in or adjacent to the nose and/or mouth of the user. Alternatively, or additionally, the detector 105 may be or comprise a rib-cage movement detector (e.g., for inductance plethysmography) configured to be affixed across the torso of the user and to provide an output signal responsive to thoracoabdominal motion and expansion and/or contraction of the rib-cage during breathing. Alternatively, or additionally, the detector 105 may be or comprise an ear plug detector configured to measure the respiratory cycle of the user via sounds and/or vibrations transmitted to the ear of the user. Alternatively, or additionally, the detector 105 may be configured to measure the percentage of oxygen or other parameters in the blood stream of the user. Alternately, or additionally, the detector 105 may be or comprise a wearable detector such as a hand or wrist detector that is configured to measure respiration by measurement of arterial tone. In an exemplary embodiment, one or more different kinds of detectors may be affixed to or positioned proximate one or more various parts of the user's body. It should be understood, however, that the detector 105 may be or comprise any type of mechanism or combination able to measure parameters of respiration or the respiratory cycle of a user and provide an electrical and/or other output signal indicative of the respiration or the respiratory cycle of the user, without departing from the principles of the present disclosure.

One or more components of the apparatus 100, whether individually or in combination, are configured to apply a stimulus to the user in response to detection by the detector 105 of apnea or other respiration disturbance. Such component(s) may be or include the detector 105, a stimulator 140, and/or another one or more components of the apparatus 100.

In an exemplary embodiment, the apparatus 100 may comprise a controller device configured to control the inducement of such stimulation in response to the detection of respiration disturbance. For example, such a controller may comprise the combination of components shown in the exemplary embodiment depicted in FIG. 1. Alternatively, the control function may be performed by the detector 105 and/or the stimulator 140, whether individually or in combination, such that the apparatus 100 may not include each or all of the discrete components depicted in the exemplary embodiment of FIG. 1. Nonetheless, although merely for the sake of clarity and example, these other components of the exemplary embodiment of the apparatus 100 shown in FIG. 1 are described below, although it is understood that the function of one or more of the components may be performed by the detector 105, the stimulator 140, and/or components of the apparatus 100 other than as described below.

The output signal produced by the detector 105 is sent to a control device 102, which is schematically depicted in FIG. 1 by the dashed lines. As described above, the control device 102, or whichever component(s) is configured to perform the function of the control device 102, is configured to receive a signal from the detector 105, analyze the signal, and then send another signal to the stimulator 140. In the exemplary embodiment shown in FIG. 1, the control device 102 comprises an amplifier 110, a wave shaping circuit 115, a pause unit 120, a monitor 125, a critical pause control circuit 130, and a signal generator 135. It should be understood, however, that the control device 102 is not limited to the embodiment depicted in FIG. 1. That is, the control device 102 may be any device or combination that is configured to receive a signal from the detector 105, analyze the signal, and then send another signal to the stimulator 140, without departing from principles of the present disclosure. For example, in an exemplary embodiment, the control device 102 and/or any other components in the apparatus 100 could be implemented as an integrated circuit and/or a central processing unit (CPU), and may utilize further components such as memory to enhance their function.

In the exemplary embodiment shown in FIG. 1, the output signal produced by the detector 105 is amplified by the amplifier 110 and then sent to the wave shaping circuit 115. The wave shaping circuit 115 is configured to change the amplified signal into a shaped signal, such as a square wave, which is indicative of the user's respiratory cycle. Thereafter, the shaped signal is sent to the pause unit 120 for monitoring. The pause unit 120 is configured to measure the duration between adjacent output signals generated by the wave shaping circuit 115 or, conversely, the duration of signal pause between consecutive output signals or pulses. During normal breathing, a visual and/or audible signal may be activated by the monitor 125. In this exemplary embodiment, the system is configured to detect an apnea, or an error, abnormality, malfunction or other disturbance in respiration, or a certain pattern in respiration. For example, such event may be a cessation or pause of respiration which exceeds a predetermined period of time. Upon detection of such event, the monitor 125 may be deactivated and/or caused to emit a signal indicative thereof. The time period may be about 10 seconds, although other time periods are also within the scope of the present disclosure.

The pause unit 120 also receives signals of adjustable duration from the critical pause control circuit 130. These signals are used by the pause unit 120 in determining whether the duration between consecutive output signals generated by the wave shaping circuit 115 have exceeded the preset period of time. If the period of time has been exceeded, the pause unit 120 activates the signal generator 135, which operates the stimulator 140 to interrupt the apnea episode or other respiration cycle disturbance and restore normal breathing of the user, possibly without fully arousing the user.

For example, the stimulator 140 may be configured to apply stimuli or send electrical, mechanical, and/or acoustic signals to one or more points of stimulation to restore normal breathing of the user without fully waking the user. The stimulation may also or alternatively be in the form of vibration. The one or more points of stimulation may include an eardrum, tympanic membrane, acoustic nerve, and/or cerebral cortex of the user. In one embodiment, the acoustic stimulation may stimulate the acoustic nerve which, in turn, stimulates respiration. However, other points of stimulation are also within the scope of the present disclosure. Moreover, the stimulator 140 may be adjusted manually or automatically according to characteristics of the user, as described below.

One or more of the functions of the previously described components may be performed by a component other than as described above. Moreover, one or more of the described components may or may not be included in the apparatus 100. In addition, the apparatus 100 may include components other than as described above or depicted in FIG. 1, including components which provide additional function or enhancements to the apparatus 100, such as a memory component. For example, a memory component may be utilized in the apparatus 100 to log the time, duration, and/or frequency of each respiration parameter and/or stimulus. Consequently, the logged information may be downloaded and/or analyzed or otherwise accessed, and may be used to report to the treating physician or for other purposes. It should be understood that the apparatus 100 may also be implemented via conventional or future-developed devices, such as may include one or more microprocessors, and may utilize wireline and/or wireless operation.

The stimulation applied by the stimulator 140 may be or comprise a sound, acoustic wave, or other signal (herein collectively referred to as a signal), or a sequence thereof. The frequency, decibel, spacing, shape and/or duration of each or all of the signals can vary, whether individually or collectively, and may be manually or automatically reconfigured based on, for example, physical or sleep characteristics of the user. The signal(s) may have one or more frequencies which fall within frequencies that are within the normal hearing range of the user, while other signals may fall within frequencies that are above or below the range for normal hearing. The signal examples and parameters listed above (e.g., frequency, duration, decibel, shape) are not an exhaustive list, and any additional parameters may be altered within the scope of the present disclosure.

The stimulation can further be configured to vary over time, and can combined with other stimulation. For example, different acoustic waves may be delivered to each ear, a combination of sounds may be applied in one ear or both ears, and/or two or more sounds may be presented in a sequence. Moreover, the stimulation may comprise one or more sound signals combined with, for example, their respective harmonic or non-harmonic frequencies in a subtractive and/or additive manner, such as to generate a harmonic signal. Such sound or resultant harmonics or non-harmonics can be within or beyond a human sound perception range, that is perceptible or imperceptible by the user, whether while in a sleep cycle or when fully aroused. Such acoustic stimulation may also be combined with other, non acoustic stimulation, such as physical or visual stimulation. In general, the specifics of the stimulation applied by the stimulator 140 is not necessarily limited within the scope of the present disclosure. In contrast, at least according to one or more aspects of the present disclosure, the stimulation applied by the stimulator 140 is configured such that respiratory cessation, when detected, is interrupted, and possibly without fully arousing the user from the sleep cycle.

Moreover, in one exemplary embodiment, the stimulation applied by the stimulator 140 may be customized per the user. Such arrangement allows the stimulation to be adjusted per the individual needs of the user, such that the stimulation can be based on characteristics of each individual user. For example, the frequency, decibels, shape and/or duration of the stimulation signal(s) may be configured based on characteristics of each individual user.

The configuration of one or more aspects of the stimulation may be manually performable by the user, the user's physician, and/or another person. Alternatively, the configuration of one or more aspects of the stimulation may be automatically performed by one or more components of the apparatus 100. In either case, the apparatus 100 may be configurable in a manner that allows tuning and configuration over time.

Similarly, the input parameters may also be configurable. For example, sensitivity of the detector 105, predetermined parameters of respiration error (such as length of respiration cessation), and/or other aspects of the detection of respiration error and/or triggering of the stimulation applied by the stimulator 140 may be manually or automatically configurable.

In embodiments in which the input parameters or the stimulation parameters are configurable, whether manually by the user, physician or sleep lab staff or automatically by one or more components of the apparatus 100, the apparatus 100 may be configured in a manner which allows these parameters to be set and/or titrated once or repeatedly, such as in a manner allowing tuning of the apparatus 100 by the user or professional personnel. Additionally, or alternatively, these parameters may be set prior to delivery of the apparatus 100 to the user or user's physician, such as before the apparatus 100 leaves the factory at which the apparatus 100 is manufactured or assembled.

The apparatus 100 may be further configured to adjust and change over time to maintain the effectiveness of the stimulation and possibly prevent habituation. This can include changes in volume, combination with other sounds, and/or other changes in the input parameters and/or stimulation parameters. Such configuration may be performed manually or automatically.

In one exemplary embodiment, the stimulation parameters may be manually or automatically configured such that the stimulation does not cause any significant changes in the patient and/or the patient's sleep architecture, except for the disturbance or interruption of the apnea or other respiration cessation. For example, the stimulation parameters may be manually or automatically configured such that the user's sleep cycle is not significantly disturbed, as possibly indicated by EEG analysis. However, at least in one exemplary embodiment, micro-arousals as known in the current literature may not constitute a significant arousal or awakening of the patient according to one or more aspects of the present disclosure.

Further, in an exemplary embodiment, the apparatus 100 may be configured to automatically detect one or more characteristics of the user and subsequently utilize the detected characteristics to titrate one or more of the above-described stimulation parameters. The titration process may be performed by a titration unit or component configured to analyze a series of apneas and responses to stimulation until optimal settings are obtained for respiration detection and/or stimulation. The titration unit or function may be a separate component of the apparatus 100, or may be integral to one or more other components of the apparatus 100.

Once optimal settings are identified, the settings may be stored and utilized during subsequent operation of the apparatus 100. In contrast, when respiration detection parameters are identified as being insufficient, and/or when effectiveness of the stimulation is identified as suboptimal, one or more algorithms may be initiated to optimize the parameters thereof to improve the effectiveness of treatment for the particular user. Such analysis may be performed periodically at predetermined time intervals or less regularly. For patients with more complex or severe sleep apnea, more frequent analyses might be recommended. These analyses may also be stored in memory of the apparatus 100 for subsequent evaluation by a medical professional.

In an exemplary embodiment, the signal applied by the stimulator 140 may be or comprise one or a sine wave, a saw-tooth wave, a square wave, and/or combinations thereof, among others. The signal may have one or more frequencies each ranging between about 250 Hz and about 8000 Hz. The signal may range between about 25 dB and about 115 dB. The signal may be a single tone, wave or other signal, or may comprise a series of such signals, each having a duration ranging between about 0.05 seconds and about 1.0 seconds. Moreover, the restoration of the user's normal breathing without waking the user may be accomplished with only acoustic stimulation, such that other forms of stimulation (e.g., those including or inducing muscle movement) are not necessary to restore normal breathing.

Figure 2:
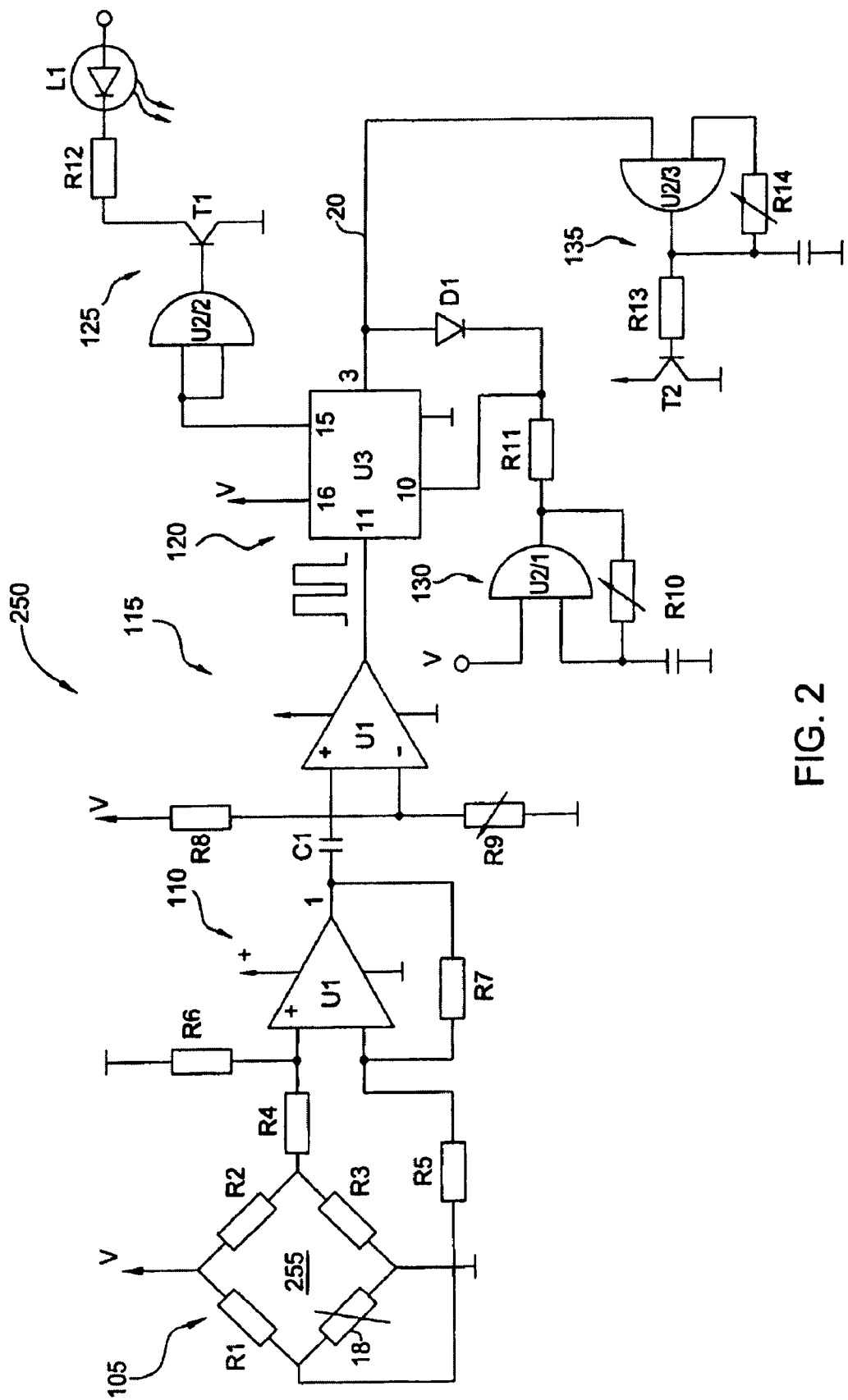
FIG. 2 is a circuit diagram of a device in accordance with one or more aspects of the present disclosure.

FIG. 2 is a circuit diagram 250 of an exemplary embodiment of the apparatus 100 shown in FIG. 1 in accordance with one or more aspects of the present disclosure. Although the circuit diagram 250 is an exemplary implementation of the apparatus 100 shown in FIG. 1, other implementations are also within the scope of the present disclosure.

In the exemplary embodiment shown, the detector 105 includes a thermistor 255 arranged in a bridge circuit having variable resistor 18 and constant resistors R1, R2, and R3. During a breathing cycle of the user, air-flow impinging on the thermistor 255 changes its resistance and thus unbalances the bridge. Thereafter, current flowing through resistors R4 and R5 will be amplified by the amplifier 110, and an oscillatory signal corresponding to the breathing cycle will be sent from the amplifier 110 via an output terminal 1. However, other embodiments within the scope of the present disclosure may utilize alternative or additional detection mechanisms.

The oscillatory signal corresponding to the breathing cycle is passed via capacitor C1 to the wave shaping circuit 115 consisting of the unit U1, resistor R8, and variable resistor R9. The shaped waveform at the output of the unit U1 is thus applied to terminal 11 of a counter U3. Each incoming pulse resets the counter U3. Simultaneously, the control circuit 130, including the unit U2/1 and the potentiometer R10, generates pulses or signals relating to the preset period of time, while the control circuit 130 applies the pulses via resistor R11 to the clock terminal 10 of the counter U3. The latter counts the number of pulses which are applied. If, within a period of time set by the resistor R9 of the shaping circuit 115, a reset pulse is not applied to the pause unit 120, there appears on its output terminal 3 an output signal. The output signal is applied via lead 20 to the signal generator 135 which includes the unit U2/3, the resistor R13, the power transistor T2, and the potentiometer R14. The generator 135 forms a signal which is applied via resistor R13 to the base of the transistor T2.

The transistor T2 conducts and activates the stimulator 140 as discussed herein. As long as a signal appears on terminal 3 of U3, the diode D1 prevents the arrival of stimuli from the control circuit 130 to the terminal 10 of U3. This state of the unit U3 will prevail until a reset signal initiated by the restoration of breathing arrives at terminal 11 of the unit. The visual and/or acoustic monitor 125 receives activating signals from terminal 15 of the unit U3. These signals are passed via unit U2/2, transistor T1, and resistor R12 to the light emitting-device (LED) L1. The LED L1 may be set to flicker during a normal breathing operation.

Figure 3:
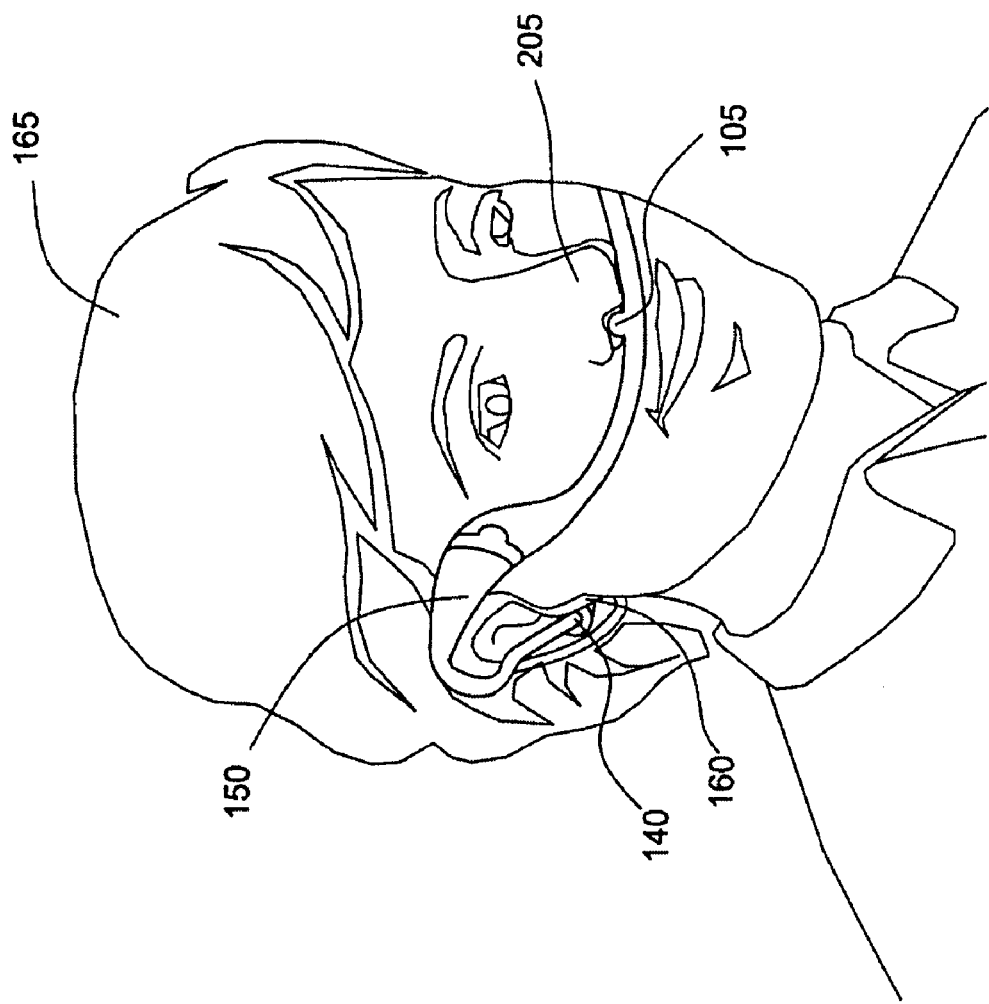
FIG. 3 is a perspective view of a nasal device disposed on a user in accordance with one or more aspects of the present disclosure.

FIG. 3 is a perspective view of a nasal-ear apparatus 150 disposed on a user 165 in accordance with one or more aspects of the present disclosure. The operation of the apparatus 150 may be substantially similar or identical to that of the apparatus 100 shown in FIG. 1, and may have a circuit diagram similar in function to the circuit 250 shown in FIG. 2. One or more aspects of the apparatus 150 and/or its components may otherwise be substantially similar to those of the apparatus described above, with the possible exceptions described below. Nonetheless, it should be understood by those skilled in the art that the apparatus 150 shown in FIG. 3 is merely one example of the possible implementation of the apparatus 100 of FIG. 1, the circuit 250 of FIG. 2, and/or other apparatus within the scope of the present disclosure.

The apparatus 150 is an exemplary embodiment of the apparatus 100, and is implemented as a goggle-, glasses- or mask-like device, wherein a detector is positioned in a portion of the apparatus 150 that is wearable around the nose, and another portion of the apparatus 150 fits within or around the ear for providing the above-described stimulation. The electronic components are positioned, for example, within the body of the goggle or externally, and this may utilize wireline or wireless communication. Thus, the apparatus 150 may be configured to fit on an ear 160 of the user 165 in a manner similar to a pair of glasses which may have one or two arms.

The detector 105 of the apparatus 150 is disposed proximate a nose 205 of the user 165, for example. In the exemplary embodiment shown in FIG. 3, the detector 105 is configured to measure the air-flow through the nose 205 of the user 165 and provide an electrical output signal indicative of the respiratory cycle of the user 165. Subsequently, the detector 105 sends an electrical output signal to a control component or function via wireless means (e.g., radio frequency) or wireline means (e.g., a cable). The control function may be performed by a device or component separate from the glasses. However, as depicted in FIG. 3, the control component and/or control function is located within the glasses, such as in one or both arms of the glasses. For example, the controller 102 of FIG. 1 may be housed within the body or arms of the glasses-like apparatus 150 or, alternatively, may be housed external to the apparatus 150 and configured to communicate with the apparatus 150 via wireless or wireline means.

One or more portions of the apparatus 150, or the entire apparatus 150, may be or comprise materials that are disposable. For example, the portion of the apparatus 150 that is positioned within or otherwise proximate the nose 205 of the user 165 may be a disposable component of the apparatus 150 that is detachable and, thus, replaceable. Alternatively, or additionally, the portion of the apparatus 150 that is positioned within or otherwise proximate the ear 160 of the user 165 may be a disposable component of the apparatus 150 that is detachable and, thus, replaceable.

Figure 4:
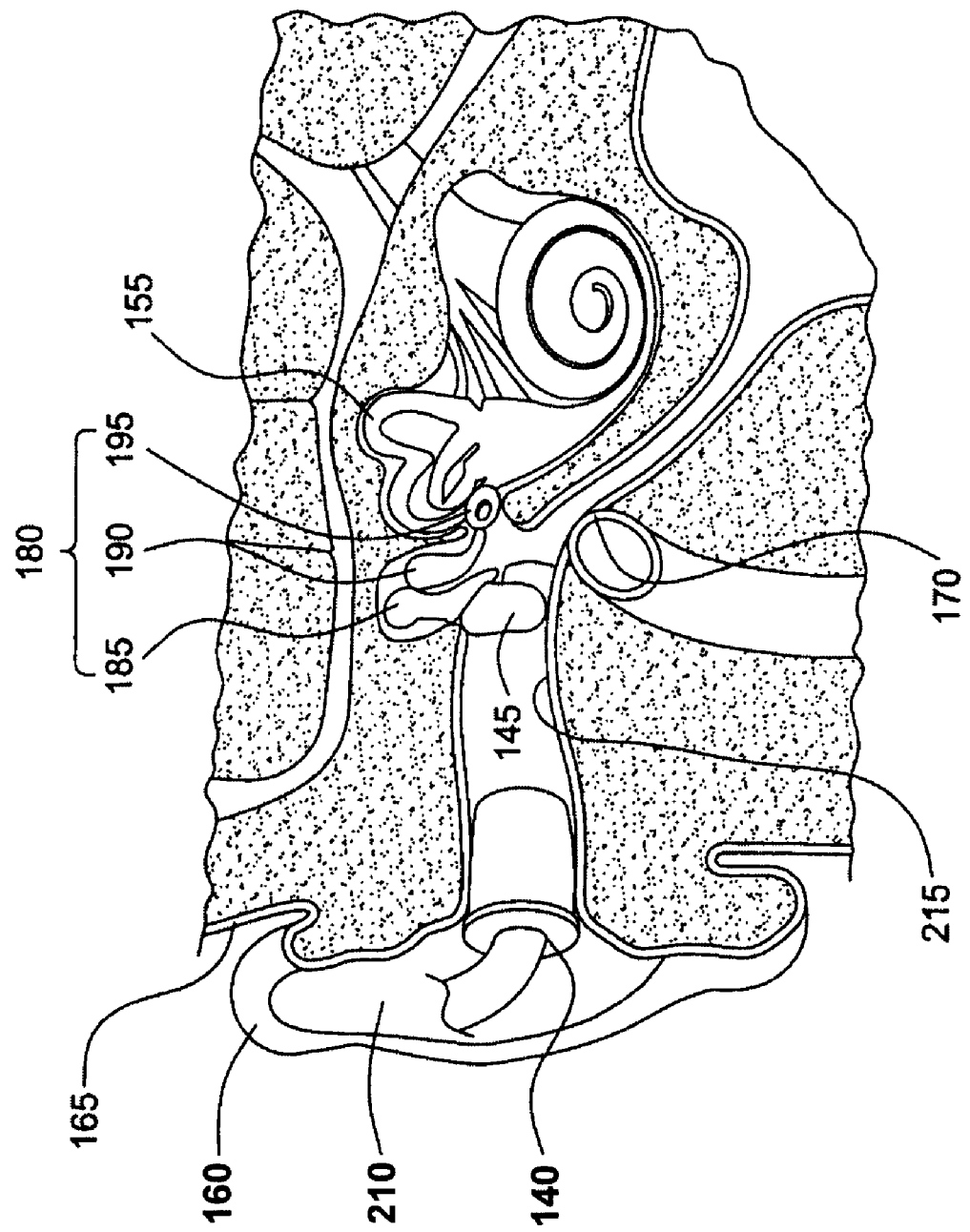
FIG. 4 is a schematic view of a stimulator device disposed in an ear of a user in accordance with one or more aspects of the present disclosure.

FIG. 4 is a schematic view of the stimulator 140 of the apparatus 150 disposed in the ear 160 of the user 165 as shown in FIG. 3. The ear 160 includes an outer ear 210, an ear canal 215 coupled to the outer ear 210, and a tympanic membrane 145 disposed near the medial end of the ear canal 215. An ossicular chain 180, located in the middle ear and disposed on the medial side of the tympanic membrane 145, couples and amplifies vibrations from the tympanic membrane 145 to the inner ear, which has a spiral structure known as the cochlea 155. The cochlea 155 converts the vibrations into nerve stimuli to the brain. The structure of the outer ear 210 provides a "funnel" to direct and amplify sound waves into the ear canal 215. The apparatus 150 may "worn" by the user such that the portion of the apparatus 150 which includes the stimulator 140 is positioned in or near the ear 160 of the user 165. Alternatively, in other exemplary embodiments, the stimulator 150 or portion of the apparatus 150 which includes the stimulator 150 may be implanted in the skin of the ear 160, or possibly attached to the lobe or other section of the ear in a manner similar to an earring.

The stimulator 140 receives signals in response to an apnea episode and/or other respiration disturbance and then applies electrical, electromagnetic, and/or acoustic signals to the ear 160 of the user 165. Where the signals are acoustic, they may be as described above. The electrical, electromagnetic, and/or acoustic signals may impact the tympanic membrane 145 and/or portions of the middle and inner ear and vibrate the ossicular chain 180, specifically the malleus 185, the incus 190, and the stapes 195. These three bones in the ossicular chain 180 act as a set of levers that amplify the vibrations received by the tympanic membrane 145. The stapes 195 is coupled to the entrance of the cochlea 155, which contains an inner ear fluid. The mechanical vibrations of stapes 195 cause the fluid to develop fluid stimuli that causes small hair-like cells (not shown) in the cochlea 155 to vibrate. The vibrations are transformed into electrical stimuli which are transmitted via neuro-pathways to the hearing center and other areas of the brain, and thereby stimulate the user 165. This stimulation, or other cortical responses, causes respiratory responses in the user 165, which results in the restoration of normal breathing for the user. Moreover, the restoration of normal breathing may be accomplished without fully arousing the patient.

Figure 5:
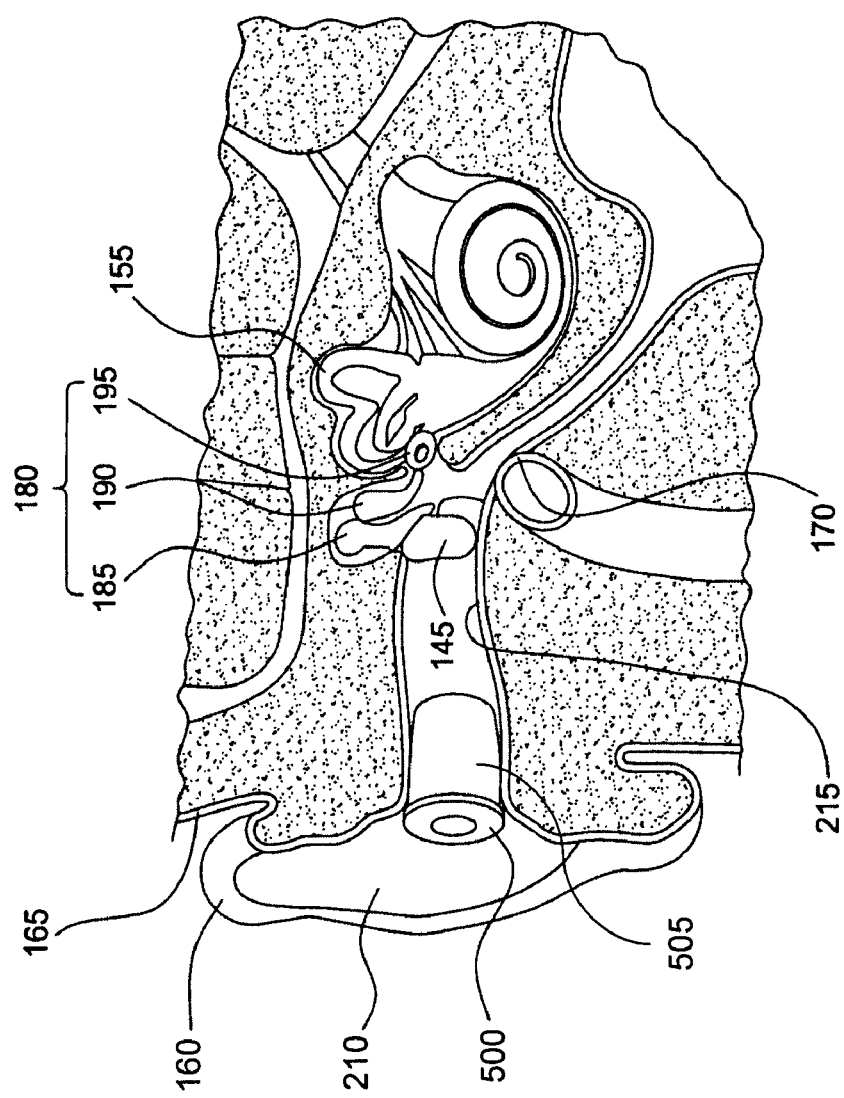
FIG. 5 is a schematic view of an ear device disposed in an ear of a user in accordance with one or more aspects of the present disclosure.

FIG. 5 is a schematic view of another embodiment of an apparatus 500 configured to be positioned within the user's ear 160 according to one or more aspects of the present disclosure. The operation of the apparatus 500 may be substantially similar or identical to that of the apparatus 100 shown in FIG. 1, and may have a circuit diagram similar in function to the circuit 250 shown in FIG. 2. One or more aspects of the apparatus 500 and/or its components may otherwise be substantially similar to those of the apparatus described above, with the possible exceptions described below. The apparatus 500 is an exemplary embodiment of the apparatus 100, and is implemented as an ear bud or ear piece configured to be wholly enclosed within a housing 505 that is positioned or implanted in or near the ear 160 of the user 165. Nonetheless, it should be understood by those skilled in the art that the apparatus 500 shown in FIG. 5 is merely one example of the possible implementation of the apparatus 100 of FIG. 1, the circuit 250 of FIG. 2, and/or other apparatus within the scope of the present disclosure.

Figure 6:
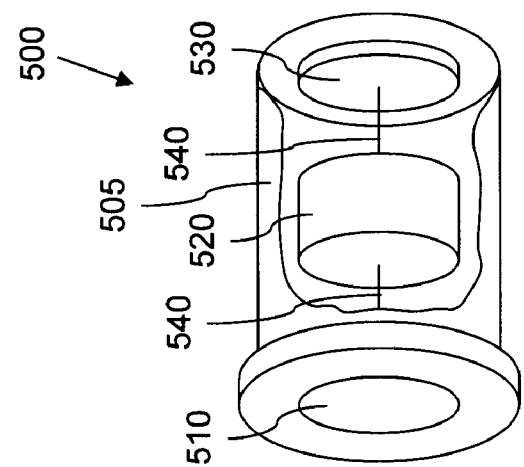
FIG. 6 is a schematic view of the device shown in FIG. 5.

FIG. 6 is a schematic view of the apparatus 500 shown in FIG. 5, with a portion of its outer housing 505 removed for clarity. The housing 505 may be substantially cylindrical or otherwise configured to be received and retained within the user's ear 160, and houses at least a portion of each of a detector 510, a control unit 520, a stimulator 530, and wires or other communicative means 540 interconnecting the control unit 520 with the detector 510 and the stimulator 530. One or more aspects of the detector 510, the control unit 520 and/or the stimulator 530 may be substantially similar or identical to those described above. For example, the control unit 520 may be substantially similar or identical in function and/or operation to the control device 102 shown in FIG. 1, and/or portions of the circuit 250 shown in FIG. 2.

The detector 510 is configured to detect the user's respiratory cycle, as in the embodiments described above. For example, the detector 510 may be configured to detect the audible sounds of the user's respiratory cycle, such as where the detector 510 is or comprises a microphone or other sound-detecting device. Alternatively, or additionally, the detector 510 may be configured to detect inaudible vibrations of the user's respiratory cycle, such as those which may be transmitted to the user's ear canal 215 through other portions of the user's ear and other body parts.

The stimulator 530 may be or comprise a speaker or other vibration-producing component configured to direct an audible or inaudible acoustic signal towards the user's tympanic membrane 145. The control unit 520 is configured utilize information received from the detector 510 to determine when the user is experiencing a sleep apnea, as described above. In response to such determination, the control unit 520 is further configured to direct the stimulator 530 to apply a stimuli to the user's tympanic membrane 145 and/or portions of the middle and/or inner ear, such as to vibrate the ossicular chain 180 and, ultimately, acoustically stimulate the user 165. This acoustic stimulation, or other cortical responses, causes respiratory responses in the user 165, which results in the restoration of normal breathing for the user. Moreover, such results may restore normal breathing without waking or otherwise interrupting or disturbing the sleep cycle of the user.

It should be evident to those skilled in the pertinent art that the present disclosure introduces an automated respiration stimulation apparatus comprising, at least in one exemplary embodiment, a detector configured to measure a respiratory cycle of a user and a stimulator configured to automatically apply a stimulation to the user's acoustic nerve to interrupt an abnormality, error, malfunction or other disturbance in the respiratory cycle of the user in response to the detection of the disturbance as indicated by the respiratory cycle measurements of the detector. The stimulator may be configured to automatically apply the stimulation to the user to interrupt the disturbance in the respiratory cycle of the user and restore respiration without causing a full arousal of the user. The apparatus may further comprise a control device configured to receive and analyze an output signal from the detector to detect the disturbance in the respiratory cycle of the user and cause the stimulator to automatically apply the stimulation to the user in response to detection of the disturbance. The apparatus may further comprise a pause unit configured to receive a signal from a wave shaping circuit. The detector may comprise at least one of a thermistor configured to be positioned proximate the user's nose, a belt configured to be positioned proximate the user's thoracoabdomen, a sensing element configured to be positioned in or proximate the user's ear, and a sensor configured to measure a blood parameter of respiration. The apparatus may further comprise a housing configured to be at least partially received within the user's ear and containing at least a portion of at least one of the detector and the stimulator. The apparatus may be configured to be completely received within the user's ear. At least a portion of at least one of the detector and the stimulator may be configured to be implanted into or attached to the user's ear. The detector and the stimulator may be integrated into a structure configured to be worn over the user's ear. The detector may be configured to be positioned proximate the user's nose or inserted into the user's nose. The stimulation may comprise acoustic stimulation. At least one operational parameter of the stimulator may be configured to be adjusted, wherein the at least one operational parameter may be selected from the group consisting of: signal frequency, signal spacing, signal duration, signal shape, signal volume and number of signals. At least one operational parameter of the stimulator may be configured to be adjusted based upon characteristics of the user in an automatic or manual manner. At least one operational parameter of the stimulator may be configured to change over time. The stimulator may be configured to continue to periodically apply the stimulation to the user's acoustic nerve until detection of a normal respiratory cycle by the detector. The stimulator may be configured to apply successive and progressive stimulation until detection of a normal respiratory cycle by the detector. The apparatus may further comprise an integrated circuit comprising at least a portion of each of the detector and the stimulator.

The present disclosure also introduces a method of stimulating respiration in a user, wherein at least one exemplary embodiment comprises detecting a respiratory cycle of the user, and acoustically stimulating the user's acoustic nerve automatically upon detection of an error in the respiratory cycle of the user. The method may further comprise adjusting the acoustic stimulation in response to the respiratory cycle of the user. The step of acoustically stimulating the user may not fully arouse the user but may still restore the user's normal respiration cycle, thereby interrupting a sleep apnea episode of the user without fully waking the user.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. An automated respiration stimulation apparatus, comprising:

a detector configured to measure a respiratory cycle of a user;

an acoustic stimulator configured to automatically apply an audible stimulation to the user's acoustic nerve to interrupt a disturbance in the respiratory cycle of the user in response to the detection of the disturbance as indicated by the respiratory cycle measurements of the detector; and a control device configured to receive and analyze an output signal from the detector to detect the disturbance in the respiratory cycle of the user and cause the stimulator to automatically apply the stimulation to the user in response to detection of the disturbance, the control device including a stimulator control circuit for selectively operating the stimulator and limiting the audible stimulation applied by the stimulator to a level that prevents full arousal of the user;

wherein the apparatus is configured to automatically apply the stimulation to the user to interrupt the disturbance in the respiratory cycle of the user without causing a full arousal of the user.

2. The apparatus of claim 1, wherein the control device further comprises a pause unit for receiving output signals from the detector and monitoring a duration between consecutive output signals.

3. The apparatus of claim 1 wherein the detector comprises at least one of a thermistor configured to be positioned proximate the user's nose, a belt configured to be positioned proximate the user's thoracoabdomen, a sensing element configured to be positioned in or proximate the user's ear, and a sensor configured to measure a blood parameter of respiration.

4. The apparatus of claim 1 further comprising a housing configured to be at least partially received within the user's ear and containing at least a portion of at least one of the detector and the stimulator.

5. The apparatus of claim 4 wherein the apparatus is configured to be completely received within the user's ear.

6. The apparatus of claim 1 wherein at least one operational parameter of the stimulator is configured to be adjusted, wherein the at least one operational parameter is selected from the group consisting of: signal frequency, signal spacing, signal duration, signal shape, signal volume and number of signals, and wherein the control unit is programmed to automatically adjust the at least one operational parameter based upon characteristics of the respiratory cycle of the user.

7. The apparatus of claim 1 wherein the stimulator is configured to, upon detection of the disturbance in the respiratory cycle, continue to periodically apply the stimulation to the user's acoustic nerve until detection of a normal respiratory cycle by the detector.

8. The apparatus of claim 1 wherein the stimulator is configured to, upon detection of the disturbance in the respiratory cycle, apply successive and progressive stimulation until detection of a normal respiratory cycle by the detector.

9. The apparatus of claim 3 further comprising an integrated circuit comprising at least a portion of each of the detector and the stimulator.

10. A method of stimulating respiration in a user, comprising:
   detecting a respiratory cycle of the user; and acoustically stimulating the user's acoustic nerve automatically upon detection of a disturbance in the respiratory cycle of the user;
   wherein the step of acoustically stimulating the user's acoustic nerve does not fully arouse the user but does restore the user's normal respiration cycle, thereby interrupting the disturbance in the respiratory cycle of the user without fully waking the user.

11. The method of claim 10 further comprising adjusting the acoustic stimulation in response to the respiratory cycle of the user.

12. The method of claim 10 wherein the step of acoustically stimulating the user's acoustic nerve comprises emitting at least one audible signal with a frequency between about 250 Hz and about 8000 Hz.

13. The method of claim 10, wherein acoustically stimulating the user's acoustic nerve comprises:
   applying a first stimulation to the user's acoustic nerve upon detection of a first disturbance in the respiratory cycle; and
   applying a second stimulation to the user's acoustic nerve upon detection of a second later disturbance in the respiratory cycle, the second stimulation having at least one operational parameter different than the first stimulation.

14. The method of claim 13, wherein the at least one operational parameter is selected from the group consisting of: signal frequency, signal spacing, signal duration, signal shape, signal volume, and number of signals.

15. The method of claim 10, further including detecting respiration parameters of the patient associated with said acoustically stimulating step to determine the effectiveness of the acoustic stimulation administered, and adjusting the acoustic stimulation level to maintain the effectiveness of the stimulation on the patient.

16. The method of claim 10, further comprising:
   providing an apparatus comprising a detector for measuring a respiratory cycle of a user and an acoustic stimulator for applying an audible stimulation to the user's acoustic nerve, the detector sized and shaped for positioning within or adjacent to the user's nose and the acoustic stimulator sized and shaped for positioning within or adjacent to at least one of the user's ears;
   positioning the apparatus on the user such that the detector is positioned within or adjacent to the user's nose and the acoustic stimulator is positioned within or adjacent to at least one of the user's ears;
   wherein detecting the respiratory cycle of the user is performed with the detector positioned within or adjacent to the user's nose; and
   wherein acoustically stimulating the user's acoustic nerve includes activating the acoustic stimulator positioned within or adjacent to at least one of the user's ears upon detection of the disturbance in the respiratory cycle of the user by the detector.

17. An automated respiration stimulation apparatus, comprising:
   a housing sized and shaped for positioning at least partially within a user's ear;
   a detector positioned within the housing and configured to measure a respiratory cycle of the user and produce output signals indicative of the measured respiratory cycle of the user;
   a control unit positioned within the housing and in communication with the detector, the control unit configured to receive the output signals indicative of the respiratory cycle of the user produced by the detector, analyze the output signals received from the detector to determine whether a predetermined amount of time has been exceeded between received output signals, and produce an activation signal when the predetermined amount of time has been exceeded;
   an acoustic stimulator positioned within the housing and in communication with the control unit, the acoustic stimulator configured to apply stimulation to the user's acoustic nerve at a frequency between 250 Hz and 8000 Hz without causing a full arousal of the user to interrupt a disturbance in the respiratory cycle of the user upon receiving the activation signal produced by the control unit.

18. The automated respiration stimulation apparatus of claim 17, wherein the detector is configured to detect audible sounds associated with the respiratory cycle of the user.

19. The automated respiration stimulation apparatus of claim 18, wherein the detector comprises a microphone.

20. The automated respiration stimulation apparatus of claim 19, wherein the control unit comprises a central processing unit.

* * * * *